United States Patent
Reynolds et al.

(10) Patent No.: US 12,011,511 B2
(45) Date of Patent: Jun. 18, 2024

(54) WALL INSTALLATION MOTION SENSOR FOR UV LIGHT SOURCE

(71) Applicant: CH Reynolds Electric Inc., San Jose, CA (US)

(72) Inventors: Charles Reynolds, San Jose, CA (US); Mark Hiura, San Jose, CA (US)

(73) Assignee: CH Reynolds Electric Inc., San Jose, CA (US)

( * ) Notice: Subject to any disclaimer, the term of this patent is extended or adjusted under 35 U.S.C. 154(b) by 0 days.

(21) Appl. No.: 18/139,317

(22) Filed: Apr. 25, 2023

(65) Prior Publication Data

US 2023/0256125 A1 Aug. 17, 2023

Related U.S. Application Data

(63) Continuation-in-part of application No. 17/987,752, filed on Nov. 15, 2022, which is a continuation of
(Continued)

(51) Int. Cl.
*A61L 2/10* (2006.01)
*A61L 9/20* (2006.01)
(Continued)

(52) U.S. Cl.
CPC ...... *A61L 2/10* (2013.01); *A61L 9/20* (2013.01); *F21S 8/046* (2013.01); *F21V 23/0471* (2013.01); *H05B 47/115* (2020.01); *H05B 47/155* (2020.01); *H05B 47/16* (2020.01); *A61L 2202/11* (2013.01); *A61L 2202/14* (2013.01); *A61L 2202/25* (2013.01); *A61L 2209/111* (2013.01); *A61L 2209/12* (2013.01); *F21Y 2113/10* (2016.08); *F21Y 2115/10* (2016.08)

(58) Field of Classification Search
CPC .......... A61L 2/10; A61L 9/20; A61L 2202/11; A61L 2202/14; A61L 2202/25; A61L 2209/111; A61L 2209/12; H05B 47/115; H05B 47/16; H05B 47/155; F21S 8/046; F21V 23/0471; F21Y 2113/10; F21Y 2115/10
See application file for complete search history.

(56) References Cited

U.S. PATENT DOCUMENTS 10,794,082 B1  10/2020  Watson et al.
10,808,964 B2  10/2020  Polidoro
(Continued)

*Primary Examiner* — Bao Q Truong

(57) ABSTRACT

A lighting fixture containing both visible light sources and UV light sources is disclosed herein. In one embodiment, the fixture is an overhead fixture. UV light can sanitize/disinfect the surrounding environment over a period of about 30-45 minutes. In this way, viruses, germs, bacteria, mold, and the like can be destroyed to clean the air and/or surfaces (e.g., furniture) of the room exposed to UV light. Accordingly, embodiments of the present invention include a physical input device, such as a wall-mounted button, switch, or wireless device, that can safely and efficiently activate a lighting assembly to produce UV light in a way that protects occupants from unintentional exposure to UV light. This configuration is especially useful in situations where the use of UV light is regulated, such as in a hospital setting.

20 Claims, 11 Drawing Sheets

Related U.S. Application Data application No. 17/364,644, filed on Jun. 30, 2021, now Pat. No. 11,541,137.

(60) Provisional application No. 63/047,795, filed on Jul. 2, 2020.

(51) Int. Cl.

| | |
|---|---|
| *F21S 8/04* | (2006.01) |
| *F21V 23/04* | (2006.01) |
| *H05B 47/115* | (2020.01) |
| *H05B 47/155* | (2020.01) |
| *H05B 47/16* | (2020.01) |
| *F21Y 113/10* | (2016.01) |
| *F21Y 115/10* | (2016.01) |

(56) References Cited

U.S. PATENT DOCUMENTS

| | | | |
|---|---|---|---|
| 11,541,137 B2* | 1/2023 | Reynolds | H05B 47/115 |
| 2008/0008620 A1* | 1/2008 | Alexiadis | F21S 4/26 |
| | | | 422/186.3 |
| 2011/0187273 A1 | 8/2011 | Summerford et al. | |
| 2015/0343104 A1* | 12/2015 | Maxik | G01J 1/42 |
| | | | 250/201.1 |
| 2017/0281811 A1* | 10/2017 | Inskeep | H05B 47/115 |
| 2018/0320872 A1 | 11/2018 | Weeks, Jr. et al. | |
| 2020/0331611 A1* | 10/2020 | Hack | A61L 2/10 |
| 2021/0404646 A1* | 12/2021 | Wang | F21V 33/0064 |

\* cited by examiner

WALL INSTALLATION MOTION SENSOR FOR UV LIGHT SOURCE

CROSS-REFERENCE TO RELATED APPLICATIONS

The present application is a continuation-in-part of U.S. patent application Ser. No. 17/987,752, with filing date Nov. 15, 2022, which is a continuation application of U.S. patent application Ser. No. 17/364,644, with filing date Jun. 30, 2021, now U.S. Pat. No. 11,541,137, which claims the benefit of U.S. Provisional Application No. 63/047,795, entitled "INDOOR LIGHTING APPARATUS INCLUDING ULTRAVIOLET LIGHT SOURCE," with filing date Jul. 2, 2020, all of which are hereby incorporated by reference in their entirety as if fully set forth below.

FIELD

Embodiments of the present invention generally relate to the field of lighting fixtures. More specifically, embodiments of the present invention relate to apparatus and methods drawn to a light fixture or lighting assembly having antiviral properties and capable of being disposed indoor or outdoor.

BACKGROUND

It is well-known that viruses, germs, bacteria, mold, and the like present a public health concern. Currently homes, businesses, and public areas are sanitized using chemicals sprayed onto surfaces and wiped away to clean the surfaces and destroy any pathogens thereon. However, this approach is time consuming, inefficient, costly, and fails to address airborne pathogens thereon that are not resting on a surface.

Recently solutions to sanitize and sterilize indoor environments incorporate the use of UV lights to destroy pathogens that may be airborne or resting on surfaces that are exposed to the UV light. However, these approaches currently rely on existing power and control systems which are not well-suited for sanitation using UV light. For example, activating UV lighting in a room occupied by people can potentially harm the occupant's skin, eyes, etc. Moreover, these lighting systems are typically controlled manually using a traditional switch which often leads to UV lights being activated during times when they are not necessarily needed or potentially dangerous to the room's occupants. A safer and more efficient light module and approach to sanitation using UV lighting are needed.

SUMMARY

A lighting fixture containing both visible light sources and UV light sources is disclosed herein. In one embodiment, the fixture is an overhead fixture. UV light can sanitize/disinfect the surrounding environment over a period of about 30-45 minutes. In this way, viruses, germs, bacteria, mold, and the like can be destroyed to clean the air and/or surfaces (e.g., furniture) of the room exposed to UV light. Accordingly, embodiments of the present invention include a physical input device, such as a wall-mounted button, switch, or wireless device, that can safely and efficiently activate a lighting assembly to produce UV light in a way that protects occupants from unintentional exposure to UV light. For example, according to some embodiments, UV lighting cannot be activated until a physical input device is manually activated (e.g., by pressing a button). This configuration is especially useful in situations where the use of UV light is regulated, such as in a hospital setting.

According to one embodiment, a lighting assembly is disclosed, including a first light source configured to produce visible light, a second light source configured to produce ultraviolet (UV) light, and control circuitry for selectively powering the first light source and the second light source, the control circuitry including a motion sensor and an input device. The control circuitry automatically deactivates the first light source and activates the second light source for a sanitation duration when the motion sensor does not detect motion for a predetermined threshold period after an input is received at the input device.

According to some embodiments, the first and second light sources are disposed within a housing and operable to be mounted as an overhead lighting assembly for installation in a ceiling of an indoor environment.

According to some embodiments, the first light source includes at least one of: a plurality of fluorescent lights and a plurality of visible light LED lights.

According to some embodiments, the second light source includes a UV LED emitter.

According to some embodiments, the input device includes a wall-mounted button and a housing, and where the motion detector is integrated into the housing.

According to some embodiments, the lighting assembly further includes a timer, and where the sanitation duration of the second light source is controlled by the timer, and a visual indicator operable to provide an indication that second light source is active.

According to some embodiments, the timer prevents activation of the second light source for a predetermined threshold period following activation of the input device even if no motion is detected by the motion sensor for a predetermined threshold.

According to some embodiments, the control circuitry further includes a normally open (NO) relay coupled to the first light source, and a normally closed (NC) relay coupled to the second light source, and where the motion sensor is operable to selectively open and close the NO relay and the NC relay.

According to another embodiment, a method of activating a visible light source and an ultraviolet (UV) light source of a lighting assembly is disclosed. The method includes detecting motion using a motion detector, closing a first relay of the lighting assembly to power the visible light source of the lighting assembly responsive to the detecting, receiving an input at an input device, and opening the first relay to deactivate the visible light source and closing a second relay to activate the UV light source responsive to the input when no motion is detected by the motion detector for a predetermined threshold time following the receiving of the input.

According to some embodiments, the lighting assembly is operable to be an overhead lighting assembly for installation in a ceiling of an indoor environment.

According to some embodiments, the visible light source includes at least one of: a plurality of fluorescent lights and a plurality of visible light LED lights.

According to some embodiments, the UV light source includes a UV LED emitter.

According to some embodiments, the input device includes a wall-mounted button and a housing, and where the motion detector is integrated into the housing.

According to some embodiments, the first relay includes a normally open (NO) relay, and where the second relay includes a normally closed (NC) relay.

According to some embodiments, the method includes receiving a second input at a switch coupled to the lighting assembly, and deactivating the visible light source and the UV light source responsive to the receiving the second input.

According to some embodiments, the predetermined threshold time is controlled by an electronic timer coupled to the lighting assembly, and further including illuminating a visual indicator during the predetermined threshold time and when the UV light source is active.

According to a different embodiment, a lighting assembly is disclosed, including a first light source configured to produce a first light type, a second light source configured to produce a second light type, and control circuitry for selectively powering the first light source and the second light source, the control circuitry including a motion sensor, a first relay coupled to the first light source, a second relay coupled to the second light source, a wireless transceiver, and a timer. The control circuitry automatically receives an activation signal from a wireless device using the wireless transceiver, starts the timer for a timer duration, opens the first relay to deactivate the first light source, and closes the second relay to power the second light source when the second relay is closed only after the timer expires, and no motion is detected by the motion sensor after the activation signal is received and over the timer duration.

According to some embodiments, the control circuitry automatically transmits an indication that the second light source is active to the wireless device using the wireless transceiver.

According to some embodiments, the wireless transceiver is operable to receive configuration data from the wireless device to configure the timer.

According to some embodiments, the wireless transceiver is operable to receive a deactivation signal that deactivates the second light source.

DETAILED DESCRIPTION

Figure 1:
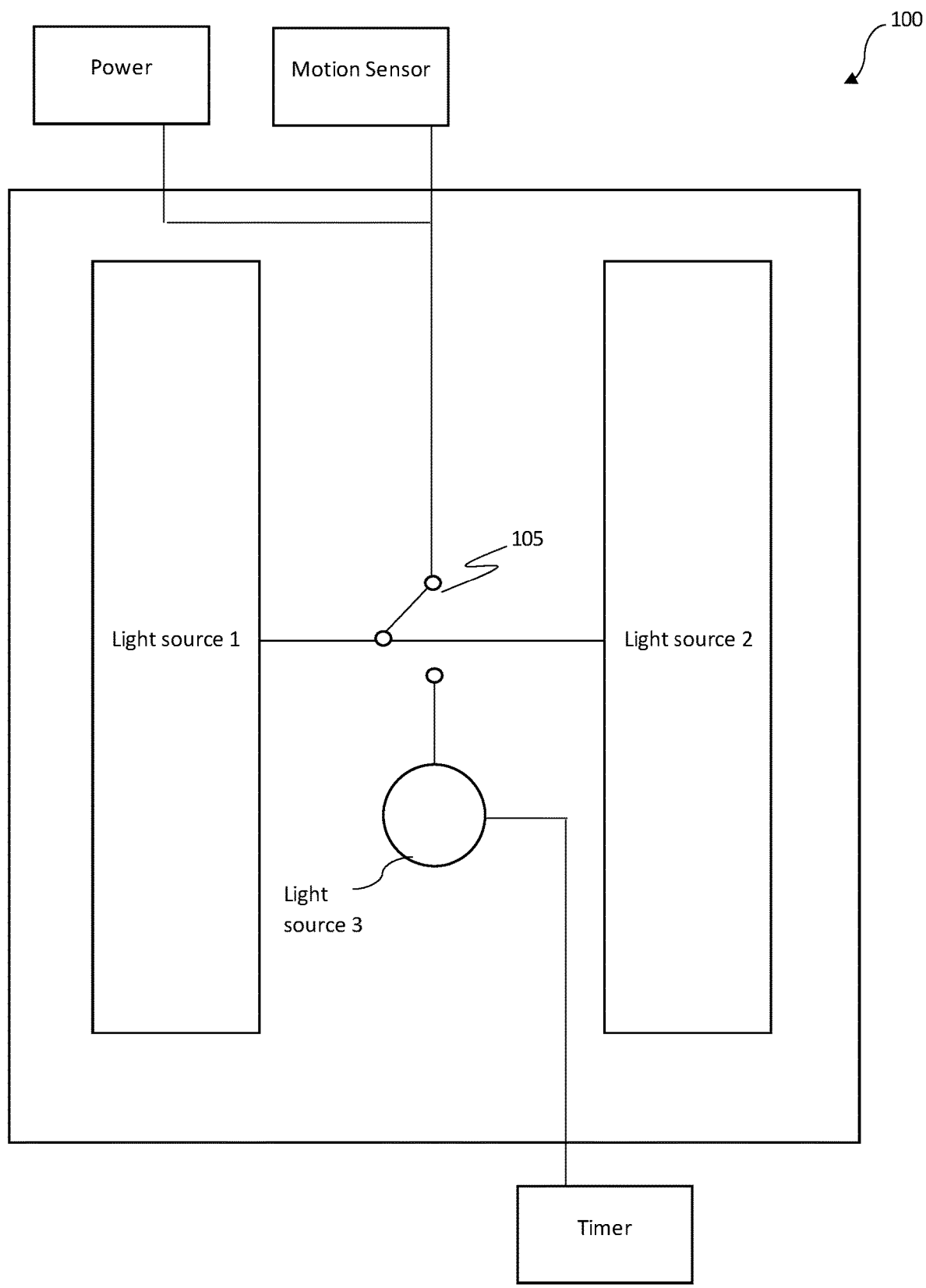
FIG. 1 depicts an exemplary lighting assembly or fixture with a presently open relay according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method. Although steps and sequencing thereof are disclosed in a figure herein (e.g., FIGS. 8-9) describing the operations of this method, such steps and sequencing are exemplary. Embodiments are well suited to performing various other steps or variations of the steps recited in the flowchart of the figure herein, and in a sequence other than that depicted and described herein.

Indoor Lighting Apparatus Including Ultraviolet Light Source

According to embodiments of the present invention, a lighting fixture or assembly is described that contains a light source that produces ultra-violet (UV) light, such as an LED, for example. UV light can be of any of a number of well-known UV source types and can sanitize/disinfect the surrounding environment if left on over a period of about 30-45 minutes. In this way, viruses, germs, bacteria, mold, and the like that are on the surfaces nearby and exposed to the UV light can be destroyed to clean the air and/or surfaces (e.g., furniture). Accordingly, embodiments of the present invention provide a controllable UV lighting assembly that can produce UV light to sanitize/disinfect an area and can be automatically disabled to prevent UV light exposure to people in the area using a motion sensor and/or other signal inputs. The lighting assembly can also provide visible light by containing visible light emitting bulbs and/or LED elements in addition to the UV light LED. In most embodiments, the visible light is provided while the UV light source is disabled since UV light is not generally advised while a room is occupied. According to some embodiments, the UV light can be triggered "on" by a motion sensor (e.g., lack of motion for a prescribed period) and the duration of UV light production is further controlled by a timer (e.g., an electronic or adjustable timer) for power savings. Since visible light emission and UV light emission within the fixture are generally on at different times, a common relay can be used to control both the UV LED and the visible light bulb(s), in one embodiment.

FIG. 1 depicts an exemplary lighting assembly or fixture 100 with a presently open relay 105 according to embodiments of the present invention. In this embodiment, the power source and motion sensor are remote to fixture 100. The relay can be controlled (opened/closed) by selectively energizing an electromagnet in the relay using a power source in one embodiment.

Lighting assembly 100 produces visible light using Light source 1 and/or Light source 2. Two visible light emitters are shown but this is exemplary only, as the light fixture 100 can include fewer or more visible light emitters. Light source 1 and Light source 2 are coupled to light couplings that both secure the lights and also conduct power to the lights; Light source 1 and Light source 2 can include fluorescent overhead lights, LED lighting arrays, or any suitable light source configured to provide visible light. Light source 3 on the other hand is a light source configured to produce UV light, such as an LED and is secured by light couplings which also conduct power to Light source 3 and can be used to secure Light source 3. Any suitable means for producing UV light can be used.

The UV light as is known cleans and/or disinfects the environment generally nearby the lighting fixture 100, e.g., about 20 feet from the fixture, over a period of exposure equal to about 30-45 minutes. The duration of the UV light produced by Light source 3 can be controlled by a timer and/or a motion detector. For instance, if no motion is detected over a period of time by the motion detector, then the UV light source can be turned on. The timer can be set for a predetermined duration (e.g., 30-45 minutes), or can include a dial or other input device that can be used to set a duration for producing UV light. During the "on" duration period of the UV light, any motion detected by the motion detector would shut off the UV light and turn off the UV "on" period. The timer signal can be used to provide the desired amount of UV light and another timer signal can also be used to prevent the UV light from being active when people are expected to enter the environment (e.g., an office, store, home, or other similar indoor environment) during work hours, for example. Saying this another way, a timer signal can be used as an override to only allow the UV "on" duration during those hours when people are not expected to be in the room, e.g., after regular work hours of an office or during expected sleep periods of a home.

Lighting assembly 100 includes relay 105 for selectively powering Light source 1 and Light source 2 to produce visible light and Light source 3 to provide UV light. The relay 105 is coupled to a power source and a motion sensor that can selectively open/close the relay when motion is detected to produce visible light (and turn off Light source 3) for the detected person/motion. For example, as depicted in FIG. 1, relay 105 is configured in the open position to provide power to Light source 1 and Light source 2. It is appreciated that Light source 3 is not powered when relay 105 is configured in this way as UV light is not advised when people are present. Therefore, in the condition when motion is detected, the lighting assembly 100 does not produce UV light and the environment is lit with visible light and is safe for occupants.

When the motion sensor does not detect motion for a prescribed period of time, the room is assumed to be empty, and the motion sensor can cause relay 105 to close. According to some embodiments, relay 105 is a normally closed relay that remains closed until toggled by the motion sensor. When relay 105 is closed, Light source 3 can be powered to produce UV light. The UV light can be further controlled by a timer signal so that the UV light is only produced when the timer is active (not yet expired) and defines a UV "on" duration. The timer can be a circuit including an input device for setting the duration of the timer, an electronically controllable timer, and/or a fixed/preset timer. The timer that defines the UV "on" duration can be integrated within the fixture 100, or it can be external to the fixture with a signal line input to the fixture. In this embodiment, the UV "on" duration does not trigger unless motion has not been detected for the prescribed period. The UV on duration will terminate upon the motion detector detecting motion.

It is further appreciated that the UV "on" duration can be further activated as described above, by another (second) timer signal which defines periods when people are not expected to be present, e.g., off work hours or sleep home hours. In this embodiment, the UV "on" duration will not start unless 1) motion has not been detected over the prescribed period AND 2) the second timer indicates a safe period, e.g., people are not expected to be present. When 1) and 2) are satisfied, in this embodiment, then the UV on period starts and will run for the timer duration unless motion is detected again. It is appreciated that the source of the second timer can be integrated within the fixture 100 or it can be generated externally with a signal supplied to the fixture 100.

According to some embodiments, lighting assembly 100 includes additional relays/circuitry so that Light source 1 and Light source 2 can be powered or activated separately. For example, only one of Light source 1 and Light source 2 can be powered to provide half of the visible light that can be produced by lighting assembly 100, and both of Light source 1 and Light source 2 can be powered at the same time to provide the full amount of visible light. In other embodiments Light source 1 and Light source 2 are also dimmable.

According to some embodiments, Light source 1 and Light source 2 are a single light source.

Figure 2:
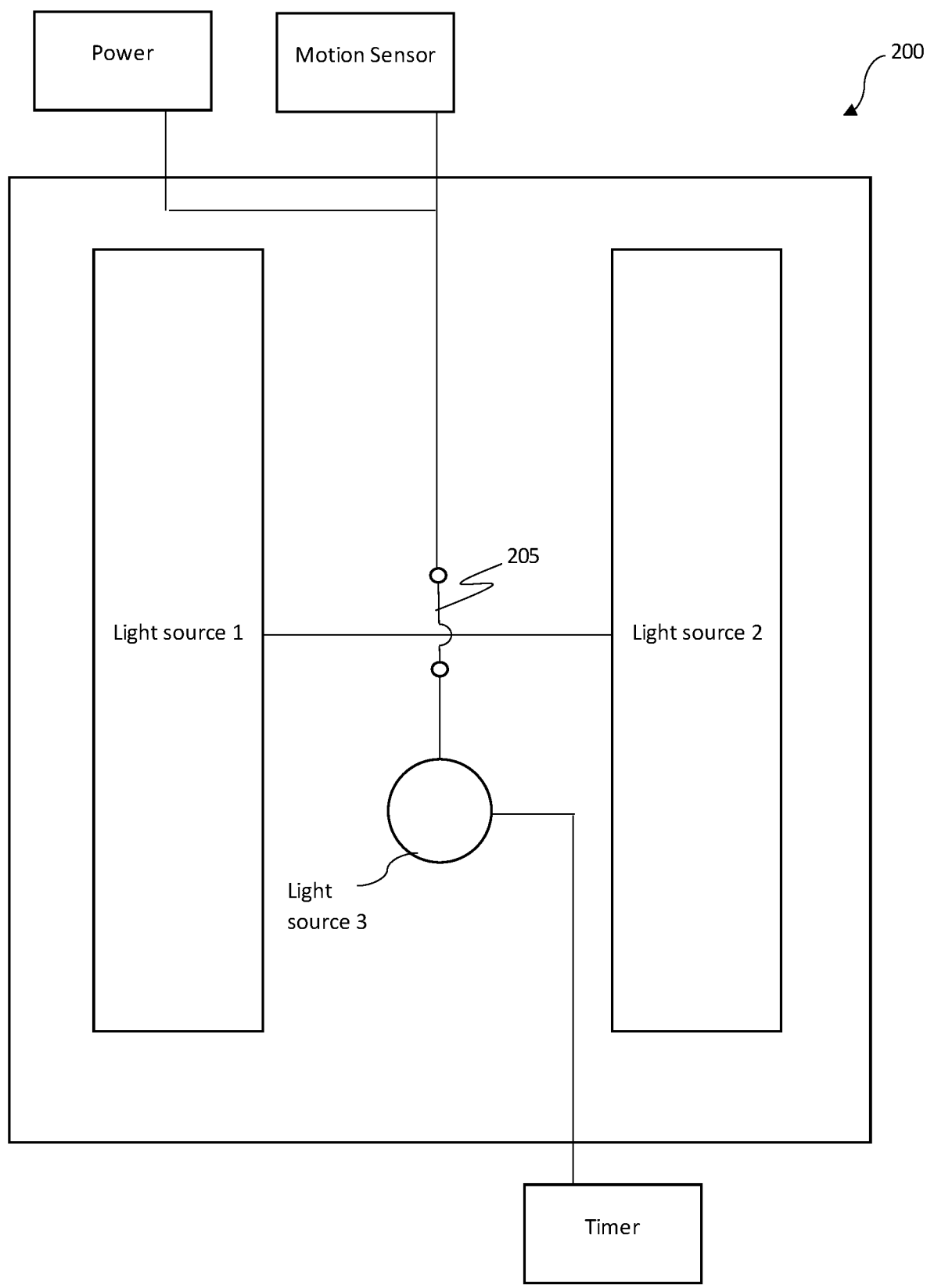
FIG. 2 depicts an exemplary lighting assembly including a presently closed relay depicted according to embodiments of the present invention.

FIG. 2 depicts a lighting assembly 200 including a presently closed relay 205 according to embodiments of the present invention. In this state, the relay 205 is closed to power/activate Light source 3 for providing UV light to clean/disinfect the environment. As mentioned above, Light source 3 can also be controlled by one or more timers for setting a duration of UV light production and a safe time period in which the UV can be activated and otherwise it is inhibited. FIG. 2 also shows the remote motion sensor.

Figure 3:
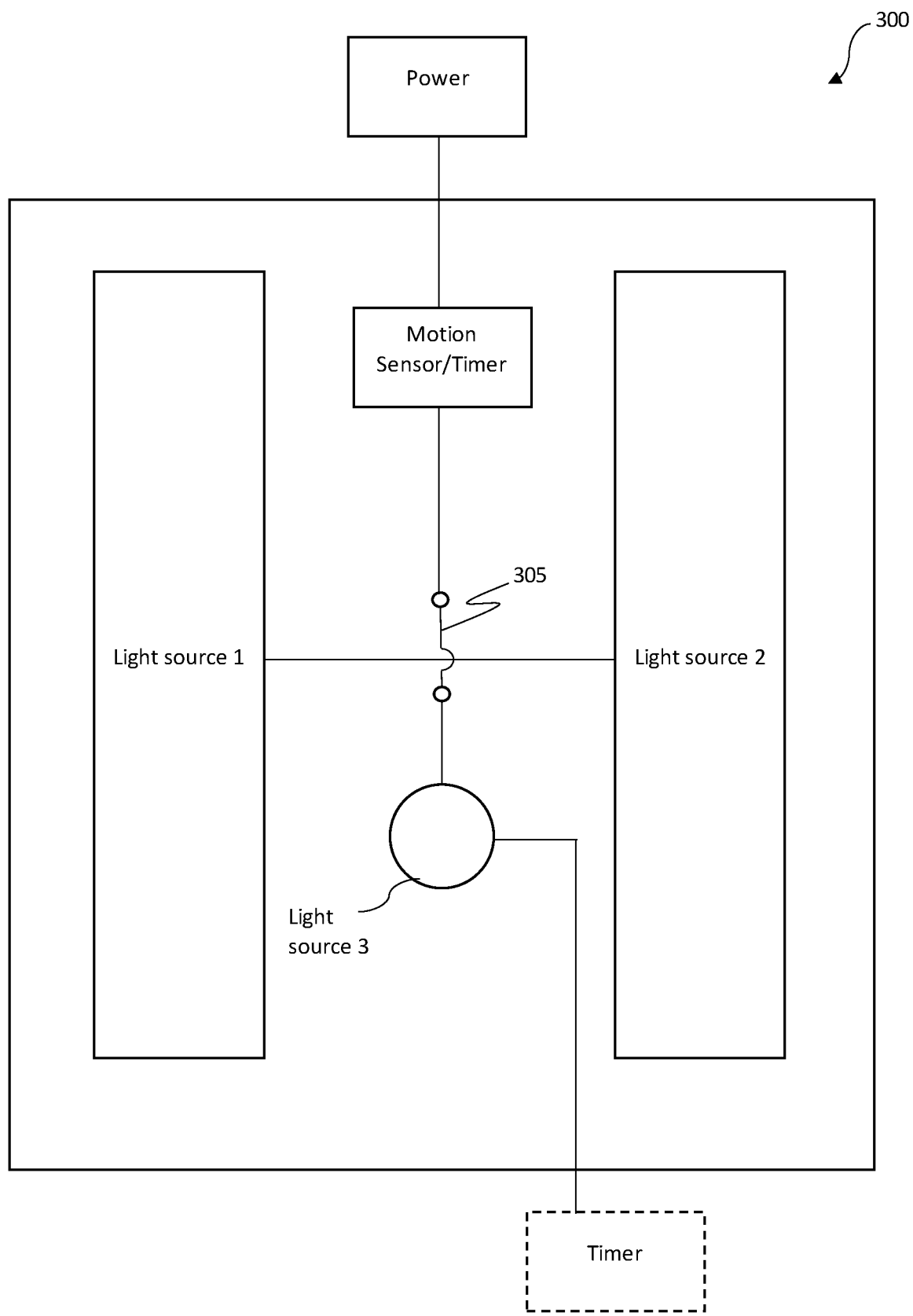
FIG. 3 depicts an exemplary lighting assembly including an integrated motion sensor/timer according to embodiments of the present invention.

FIG. 3 depicts a lighting assembly 300 including an integrated motion sensor/timer according to embodiments of the present invention. The motion/sensor timer is powered by an external power source and uses a motion sensor internal to the lighting assembly 300. The internal motion sensor can activate Light source 3 to provide UV light when no motion is detected over a prescribed period by closing relay 305, and can disable Light source 3 when motion is detected by opening relay 305. The motion sensor can include an integrated timer for controlling a duration of UV light production, e.g., the UV "on" duration, or can use a remote timer, for example, using wireless electronic communication (e.g., Wi-Fi, Bluetooth, etc.). The lighting assembly 300 can optionally include an internal second timer for controlling or defining the safe period in which the "on" duration of UV light produced by Light source 3 is allowed as discussed above with regard to FIGS. 1-2.

Figure 4:
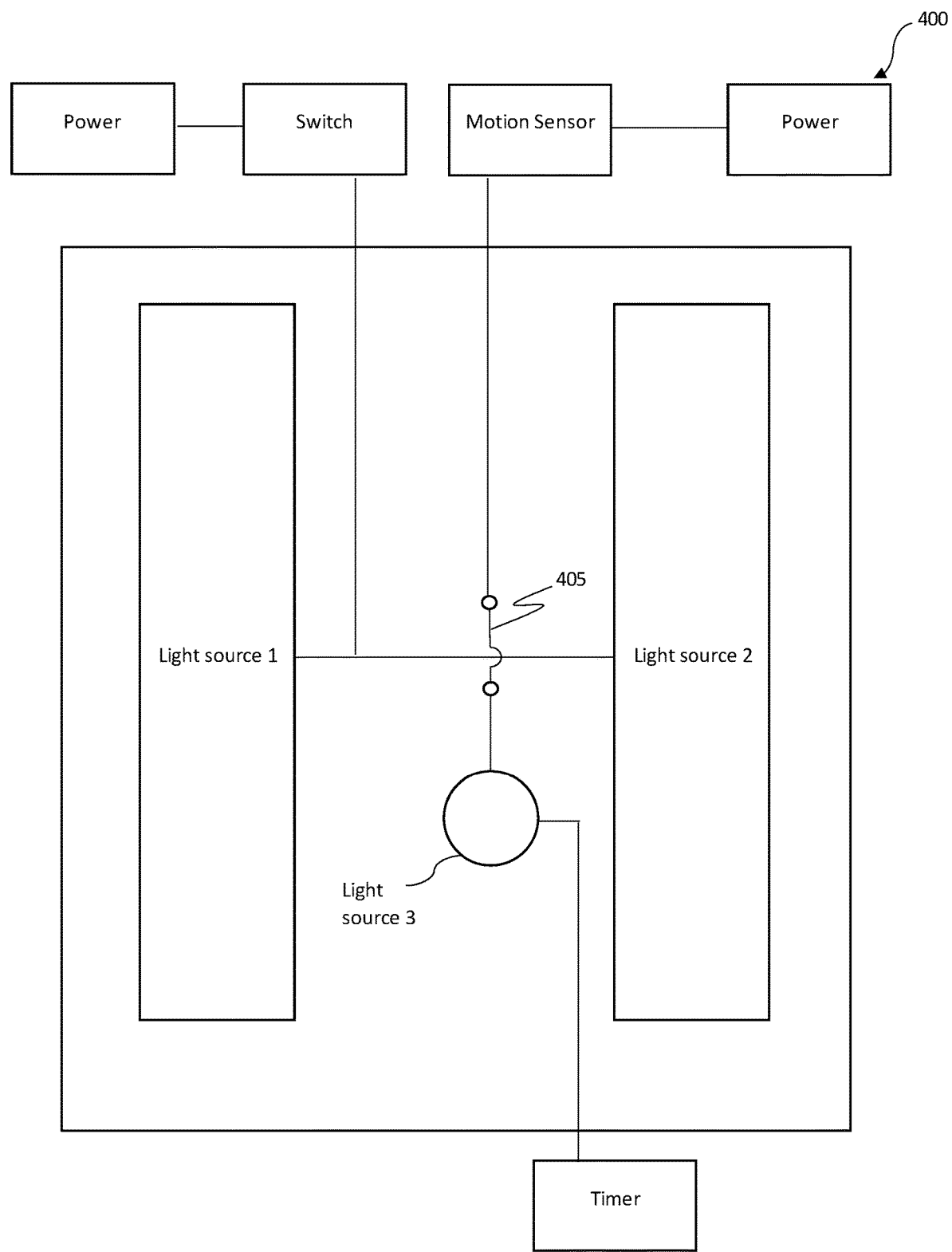
FIG. 4 depicts an exemplary lighting assembly including an external switch for controlling lighting assembly according to embodiments of the present invention.

FIG. 4 depicts a lighting assembly 400 including an external switch for controlling lighting assembly 400 according to embodiments of the present invention. The external switch is powered to turn Light source 1 and Light source 2 on and off selectively and/or to provide dimming. The motion sensor is powered separately from the external switch and selectively provides power to Light source 3 for producing UV light when relay 405 is closed. The motion sensor can activate Light source 3 to provide UV light (when no motion is detected after a prescribed period of time) by closing relay 405, and can disable Light source 3 when motion is detected (or when the "on" duration of UV light expires) by opening relay 405. As mentioned, the UV light can be further controlled by a timer so that the UV light is only produced when the timer is active (not expired). The timer can be a circuit including an input device for setting the duration of the timer, an electronically controllable timer, and/or a fixed/preset timer.

The embodiment depicted in FIG. 4 can include additional relays/circuitry to prevent lighting assembly 400 from receiving power from both power sources at the same time. According to some embodiments, the different power sources provide different voltages (e.g., 120V, 277V, low voltage, etc.) as the visible light emitters can operate at different voltages from the UV light emitter (Light source 3).

According to another embodiment, an overhead lighting fixture includes a frame, power couplings ("first power couplings") coupled to said frame and for physically retaining and powering a plurality of visible lights, and another set of power couplings (second power couplings) coupled to said frame and for physical retaining and powering a UV light. The overhead lighting fixture also includes a power input and a relay coupled to said power input and for selectively providing power to said first and second power couplings. The overhead lighting fixture can selectively provide power to the one power coupling and disable power to the other power coupling. The overhead lighting fixture can include a motion detector input for receiving a motion detector signal, and a timer input for receiving a timer signal, said timer signal is triggered to start upon said motion detector signal indicating no motion for a prescribed period. The relay is controlled to provide power to the first power coupling and disable power to said second power couplings when said motion detector signal indicates motion, and said relay is controlled to provide power to said second power coupling and disable power to said first power couplings when the motion detector signal indicates no motion and said timer has not expired.

According to some embodiments, the timer and the motion detector are integrated into the overhead lighting fixture.

According to some embodiments, the overhead lighting fixture includes another timer input (second timer input) to receive a second timer signal which is an override and indicates a safe period in which said second couplings can be enabled. The relay is controlled to provide power to the second power coupling and to disable power to the first power couplings when the motion detector signal indicates no motion, the timer has not expired, and the second timer signal is active (not expired). According to some embodiments, the lighting fixture includes a controller to control the relay. When motion is detected, the controller can provide power to the first power couplings and disable power to the second power couplings. The controller can provide power to the second power couplings when no motion is detected for a period of time, the timer input is active, and the second timer signal indicates that it is safe to provide power to the second power couplings. The controller can reset the first timer when no motion is detected for a prescribed period of time and the second timer indicates that it is safe to provide power to the second power couplings.

According to some embodiments, multiple lighting assemblies are used in conjunction. For example, multiple lighting assemblies can be installed in the same room and controlled by a single timer and/or motion sensor. Depending on the size of a room and the strength of the UV emitter, a determination can be made as to the number of lighting fixtures (and placement thereof) that a particular room requires for adequate sanitation. It is appreciated that the dimensions of the lighting fixtures in accordance with embodiments of the present invention can be sized such that they are analogous to commercially available office lighting fixtures.

According to some embodiments, the UV light source is customized to kill viruses, germs, bacteria, and/or mold using a specific frequency of UV light or a specific duration of exposure.

Figure 5:
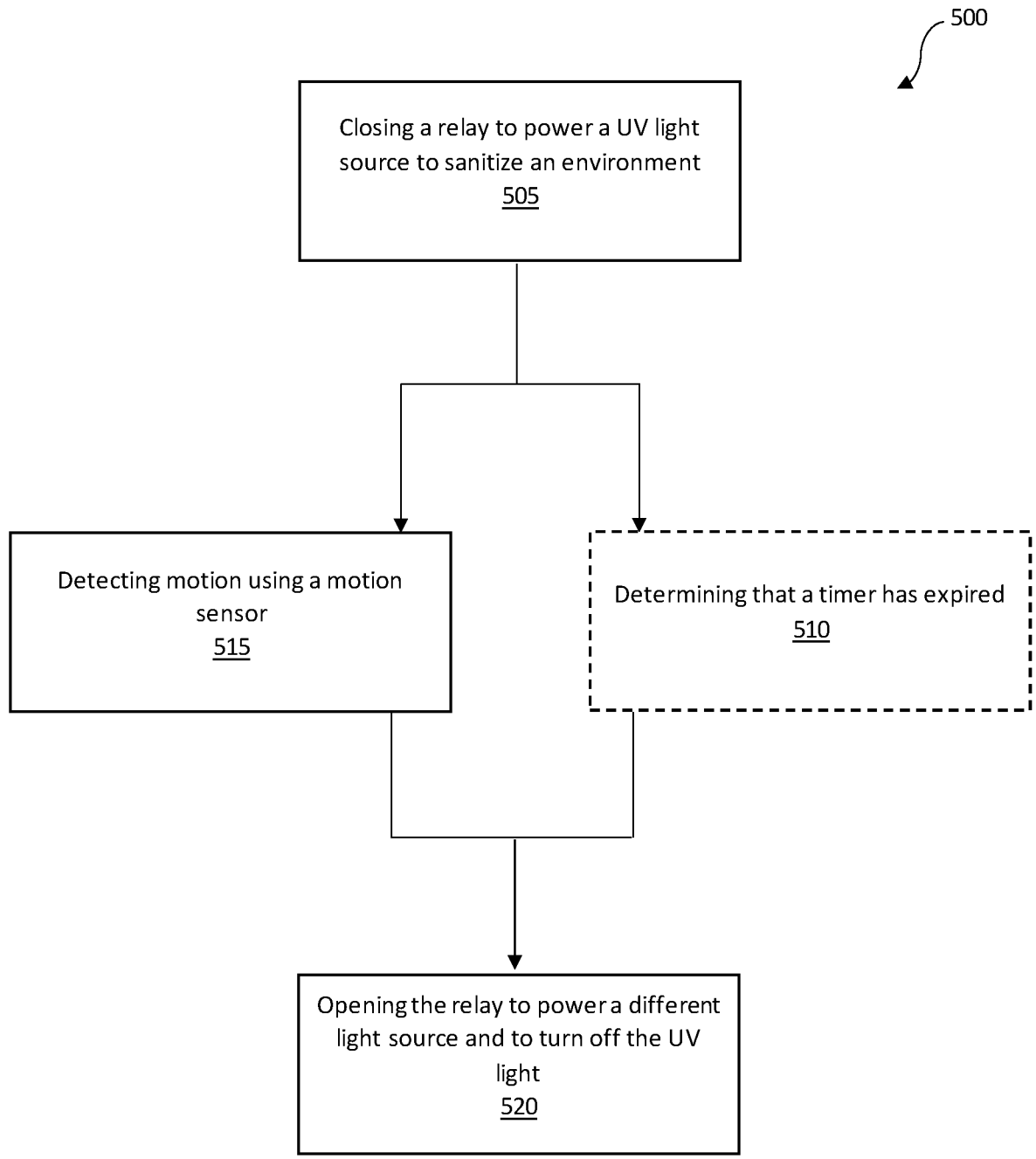
FIG. 5 depicts an exemplary sequence of steps of a process for automatically disabling a UV light source in a lighting assembly to prevent exposure of UV light to occupants according to embodiments of the present invention.

FIG. 5 depicts an exemplary sequence of steps of an electronically controlled process 500 for automatically disabling a UV light source in a lighting assembly to prevent exposure of UV light to occupants according to embodiments of the present invention. The lighting assembly can include an overhead lighting assembly having both visible and UV light sources and installed in a home, store, or office building, for example. Process 500 can be computer or electronic controlled, e.g., by a state-machine, processor, microcontroller, combinatorial logic, sequential circuits, or any suitable electronic control mechanism or combination of the above.

At step 505 of process 500, a relay of the lighting assembly is closed to power a UV light source (e.g., an LED) during a detected on period for UV light exposure. The UV light produced by the UV light source cleans and/or disinfects the surrounding environment (e.g., room), for example, to kill viruses, bacteria, germs, mold, etc. Step 505, for instance, can be triggered after a prescribed period of non-motion detected by a motion detector and measured by an on timer. Alternatively, step 505 can be triggered by an external signal indicating a safe period in which UV light can be exposed within a room. Alternatively, step 505 can be triggered by a combination of the above.

The duration of the UV production of Light source 3 is optionally controlled by a timer. The timer can be set for a predetermined duration (e.g., 30-45 minutes), or can include a dial or other input device that can be used to set a duration for producing UV light. The timer can be used to provide the desired amount of UV light and to prevent the UV light from being active when people are expected to enter the surrounding environment (e.g., an office, store, home, or other similar indoor environment). According to embodiments where the duration of the UV production of Light source 3 is controlled by a timer, at step 510, the lighting assembly determines that the timer has expired and enters step 520. According to some embodiments, the timer is included in the motion sensor. Alternatively, the timer can be external to the light fixture.

At step 515, while in the UV on duration, the motion sensor detects motion near the lighting assembly. The motion can indicate the presence of an occupant in the room where the lighting assembly is installed, or the presence of a person relatively close to the lighting assembly, for example. When motion is detected, step 520 is entered.

At step 520, responsive to the detected motion (step 515) or the expiration of a timer (step 510), the relay is opened to power a second light source (e.g., Light source 1 and/or Light source 2 depicted in FIGS. 1-4) and the UV Light source 3 correspondingly is turned off.

Figure 6:
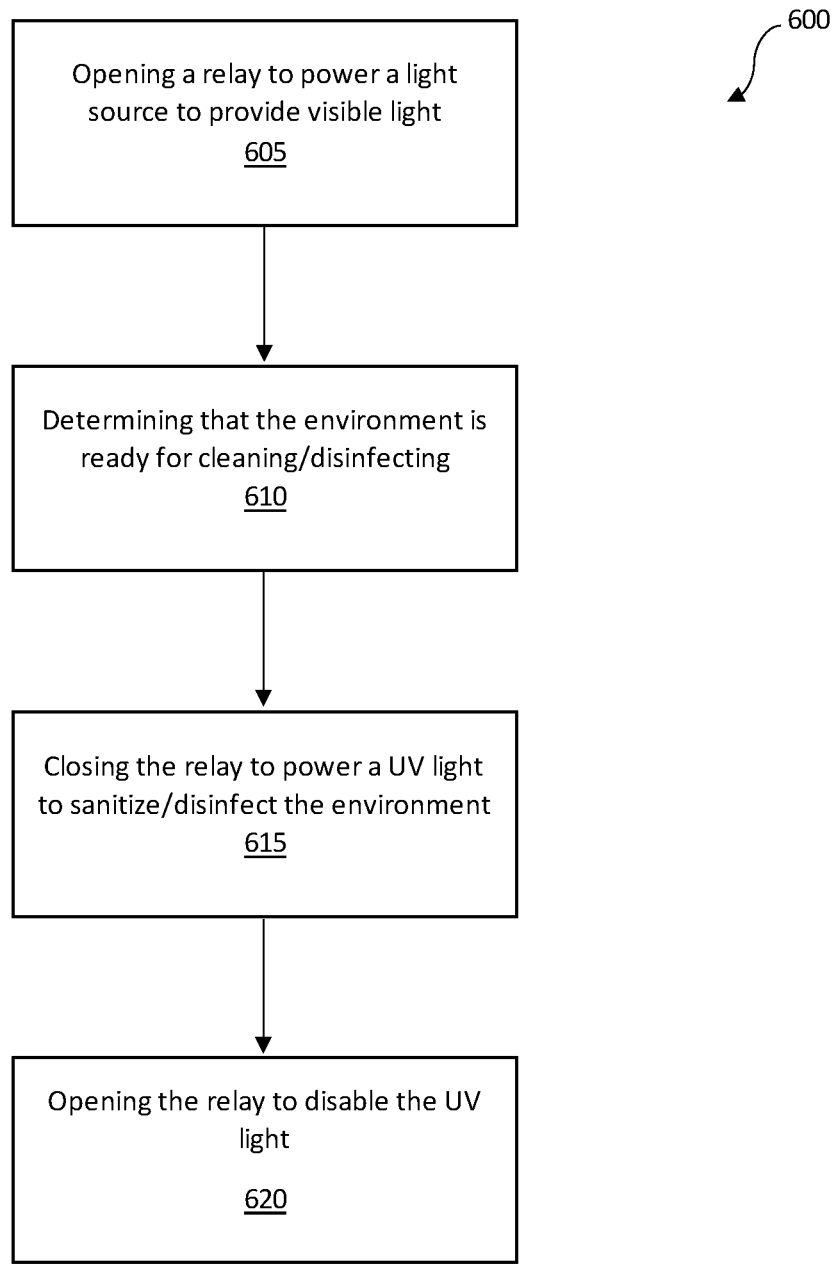
FIG. 6 depicts an exemplary sequence of steps of a process for automatically cleaning/disinfecting an environment using UV light using a lighting assembly and a motion detector according to embodiments of the present invention.

FIG. 6 depicts an exemplary sequence of steps of a process 600 for automatically cleaning/disinfecting an environment (e.g., room) using UV light using a lighting assembly and a motion detector according to embodiments of the present invention. The lighting assembly can be overhead lighting disposed in a home, store, or office building, for example. Process 600 can be computer or electronic controlled, e.g., by a state-machine, processor, microcontroller, combinatorial logic, sequential circuits, or any suitable electronic control mechanism or combination of the above.

At step 605, a relay of the lighting assembly is opened to power a light source that produces visible light. Step 605 can be triggered, e.g., by a light switch being manually selected to the on position and/or by a motion sensor sensing motion within a room.

At step 610, the lighting assembly determines that the environment is ready for cleaning/disinfecting. For example, step 610 can include determining that a timer is active (not yet expired). Moreover, step 610 can include a motion sensor determining that no motion has been detected in the room for a prescribed period of time.

At step 615, the relay is closed to power a UV light source (e.g., LED) that produces UV light to clean/disinfect the environment. At step 615 the visible light emitters can also be turned off. The UV "on" duration at step 615 can be timer based or could terminate upon motion being detected. Further, the UV "on" duration could be inhibited so that it only is triggered when the above is true and further when a secondary timer override indicates a safe period in which sanitation can take place.

At step 620, the relay is opened to disable the UV light indicating the end of the UV "on" duration. Step 620 can also include powering the visible light source(s) to produce visible light. Step 620 can be performed responsive to determining that a timer has expired or that motion has been detected by the overhead lighting assembly (e.g., by a motion sensor thereof).

Indoor Lighting Apparatus Including Ultraviolet Light Source with Normally Open and Normally Closed Relays and Activation Button Further embodiments of the present invention include a lighting assembly with a physical input device, such as a wall-mounted button, switch, or wireless device, that can safely and efficiently activate the lighting assembly to produce UV light in a way that protects occupants from unintentional exposure to UV light. For example, according to some embodiments, UV lighting cannot be activated until a physical input device is manually activated (e.g., by pressing a button). This configuration is especially useful in situations where the use of UV light is regulated, such as in a hospital setting. In particular, new lighting requirements have been imposed by the State of California and other jurisdictions that require compliance with existing Energy Codes. For these reasons, the use of lighting systems that automatically turn on at certain times may not be possible due to regulatory requirements regarding occupational safety. Some embodiments of the present invention can be integrated into existing building management systems (BMS) that automatically override the lighting controls to automatically deactivate the lighting system at specific times, such as when a Title 24 sweep is performed.

Figure 7:
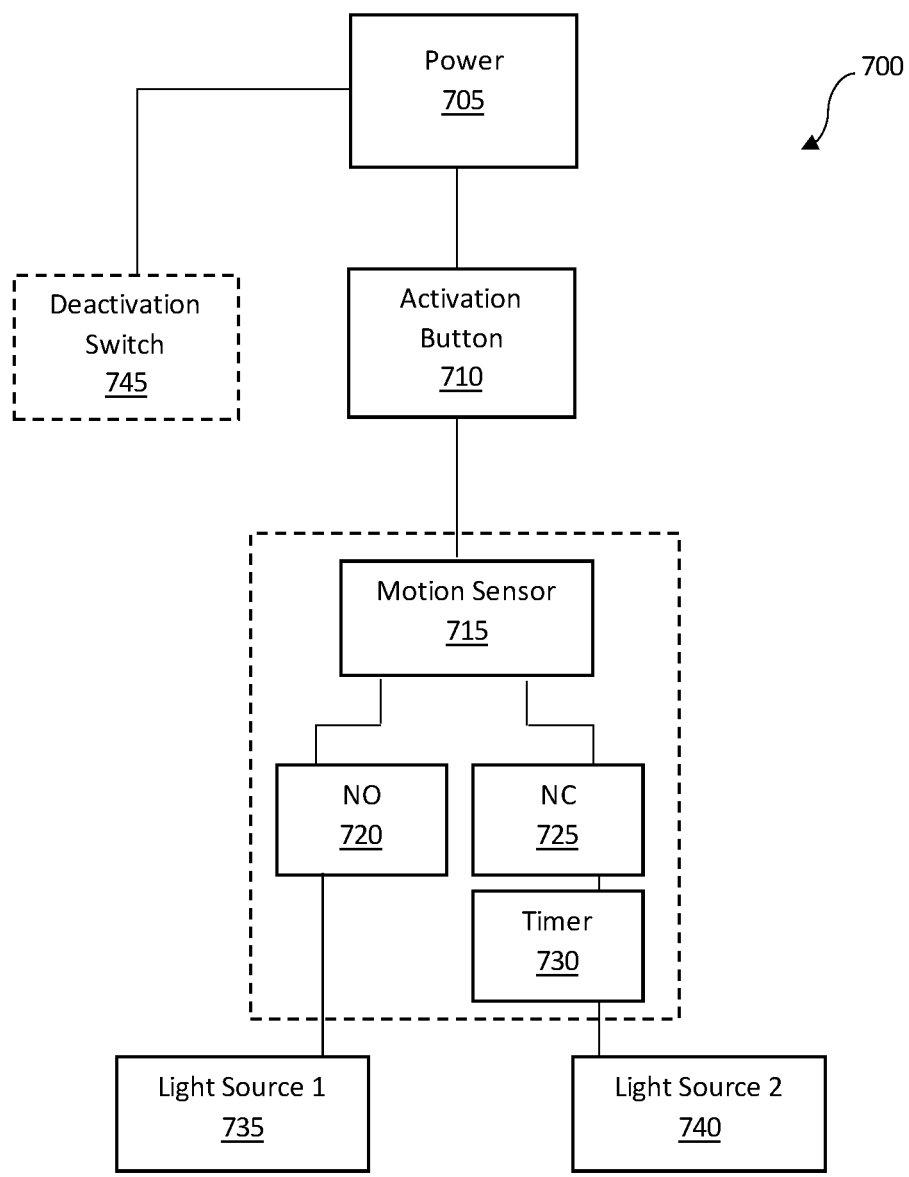
FIG. 7 depicts an exemplary lighting assembly including motion-controlled relays and for controllably emitting indoor light to sanitize a room and protect occupants thereof from unintentional exposure to UV light according to embodiments of the present invention.

FIG. 7 depicts a block diagram of an exemplary lighting assembly 700 including motion-controlled relays 720 and 725 for controllably emitting indoor UV light (e.g., in hospital room, conference room, etc.) to sanitize a room and protect occupants thereof from unintentional exposure to UV light according to embodiments of the present invention. The lighting assembly 700 can be readily integrated into existing lighting systems and can include wired and wireless components according to embodiments.

Lighting assembly 700 receives power from power source 705 to drive Light source 1 (735) and Light source 2 (740). Light source 1 and Light source 2 can include several individual lights, different banks of lights, lighting arrays, etc. Light source 1 is operable to produce light that is visible for illuminating the room, and that is safe for occupants. Light source 2 is configured to provide UV light for sanitizing surfaces of the room. However, activating Light source 2 when the room is occupied may be dangerous to occupants, and therefore NO relay 720 and NC relay 725 are coupled to both a motion sensor 715 and a physical activation button 710 to prevent activation of UV light sources when the room is occupied. The motion sensor and the activation button can be mounted on a wall of the room (e.g., near an entrance/exit of the room), and can be housed together or separately.

Light source 1 is coupled to NO relay 720 that is normally open and therefore Light source 1 is not normally powered. When motion inside the room is detected by motion sensor 715, NO relay 720 closes to conduct power from power source 705 to Light source 1 to illuminate the room using visible light. Light source 2 is coupled to NC relay 725 that is normally closed. When motion inside the room is detected by motion sensor 715, the room is assumed to be occupied NC relay 725 opens to stop conducting power from power source 705 to Light source 2 so that no UV light is emitted from lighting assembly 700.

Light source 2 is activated by activation button 710. For safety reasons, Light source 2 will not emit UV light until activation button 710 is pressed. Typically, activation button 710 is pressed after the occupants have left the room, or are in the process of leaving the room.

According to some embodiments, a physical interaction with activation button 710 activates a timer 730 coupled to NC relay 725. Timer 730 is typically configured to wait for a short duration of 4-5 minutes after activation button 710 is pressed, after which the UV lights are activated to sanitize the room (unless motion is detected by motion sensor 715, in which case the UV light is not activated). In other words, detected motion will override the UV emission to turn off the UV light source. The UV lights are activated by timer 730 for a duration of approximately 30-45 minutes to sanitize the room of germs, such as viruses, fungus, and bacteria, that may be present in the room and the UV lights shut off at the timer expiration. After the timer expires, lighting assembly 700 turns off until motion is detected, in which case Light source 1 is activated, or until activation button 710 is pressed again to restart the sanitizing UV light when no motion is detected for a predetermined threshold.

Activation button 710 can be a wall-mounted switch, such as a single-pole double-through switch that can toggle power to NO relay 720 and NC relay 725, or a wireless device that communicates wirelessly with motion sensor 715, such as a Bluetooth or Wi-Fi device. According to some embodiments, activation button 710 includes a visual indicator, such as an LED, that turns on to indicate that UV light is currently being emitted to sanitize the room. The visual indicator also aids in distinguishing the activation button from a conventional light switch. Moreover, the visual indicator can produce different colors depending on the status of the UV light source. For example, the visual indicator can be a green light that becomes a red light when the UV light source is active. According to other embodiments, the visual indicator is disposed outside of the room, or is transmitted wirelessly to a wireless device via Bluetooth or Wi-Fi, for example. The wireless device can also send configuration data to the lighting assembly to configure timer values, lighting schedules, etc. According to some embodiments, lighting assembly 700 optionally includes deactivation switch 745 that can be toggled to immediately stop the production of UV light, for example, if the room is determined to be occupied or is soon to be occupied, in which case UV light should be deactivated. According to other embodiments, deactivation switch 745 is not used, and a deactivation signal can be received wirelessly from a wireless device using Wi-Fi, Bluetooth, etc.

Figure 8:
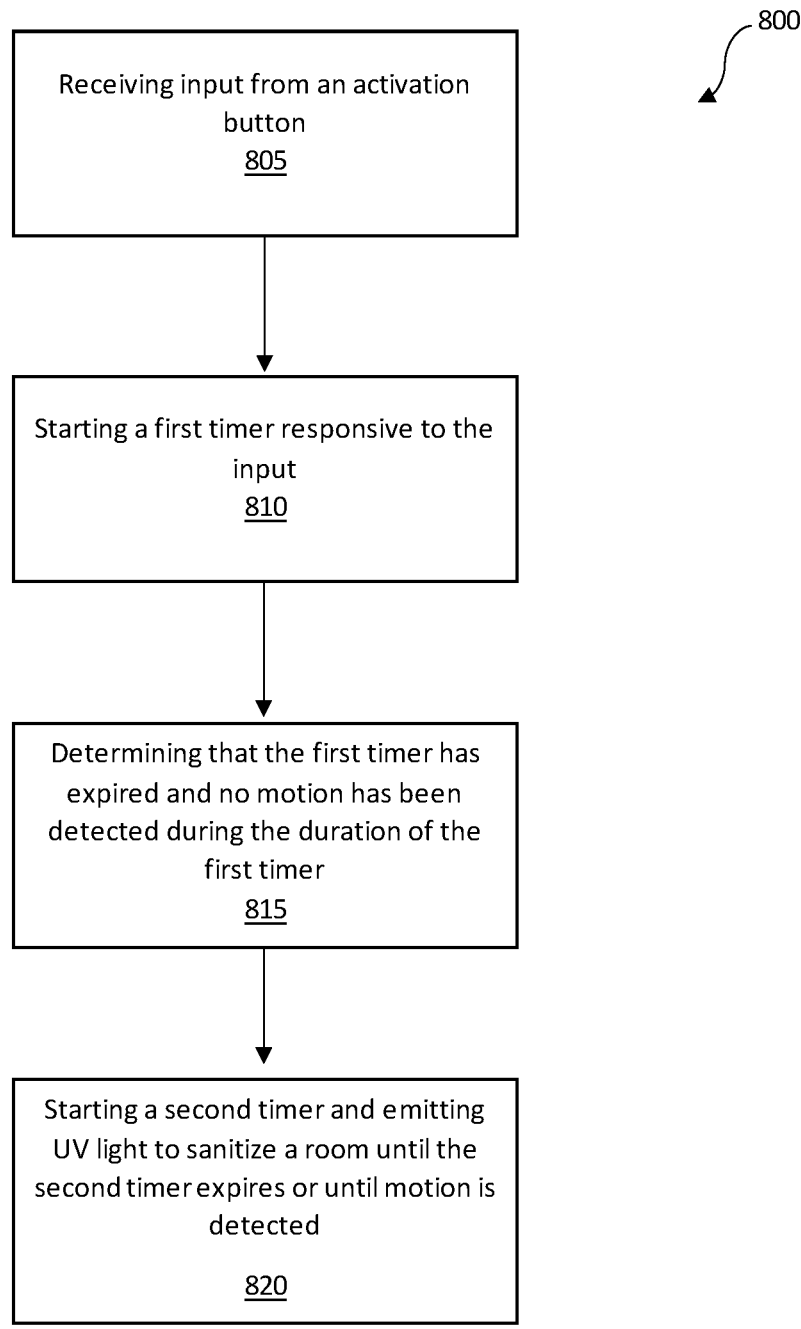
FIG. 8 depicts an exemplary sequence of steps of a process for automatically cleaning/disinfecting a room using a motion detector and a physical input coupled to multiple light sources according to embodiments of the present invention.

FIG. 8 depicts an exemplary sequence of steps of a process 800 for automatically cleaning/disinfecting a room (e.g., an office, bedroom, hospital room, etc.) using a motion detector and a physical input device (e.g., an activation button) coupled to multiple light sources. The lighting assembly can be overhead lighting and can include NO and NC relays for selectively powering a UV light source and a visible light source. Process 800 can be computer or electronic controlled, e.g., by a state-machine, processor, microcontroller, combinatorial logic, sequential circuits, or any suitable electronic control mechanism or combination of the above.

At step 805, input is received from an activation button coupled to a motion detector that controls a UV light source and a visible light source. The activation button is used to activate the UV lights in coordination with the motion sensor and one or more timers to prevent unintended UV light exposure to occupants thereof. In normal expected operation, the activation button is pressed as the last of the room occupants leave the room.

At step 810, a first timer is activated in response to the input received at step 805. The first timer may be considered a countdown that provides room occupants with sufficient time to clear the room (typically a few minutes) before the UV lights are activated. If motion is detected before or after the timer expires, the UV lights do not activate. According to some embodiments, the timer resets as soon as the motion detector stops detecting motion. According to other embodiments, the activation of the UV lights is canceled if motion is detected during while the countdown timer is active.

At step 815, it is determined that the first timer has expired and no motion has been detected for the duration of the first timer.

At step 820, the UV light is activated (e.g., by closing an NC relay) responsive to the determination of step 815. Step 820 can include starting a second timer measuring a sanitation period, after which the UV lights are again deactivated. The second timer typically has a duration of 30-45 minutes ("sanitation period") to substantially sanitize the room from germs, such as viruses, bacteria, mold, etc. The UV light can also be deactivated immediately when motion is detected in the room, or when an optional deactivation switch is thrown. At the end of the sanitation period, detected motion in the room activations the visual light source similar to a conventional motion activated light, see FIG. 9.

Figure 9:
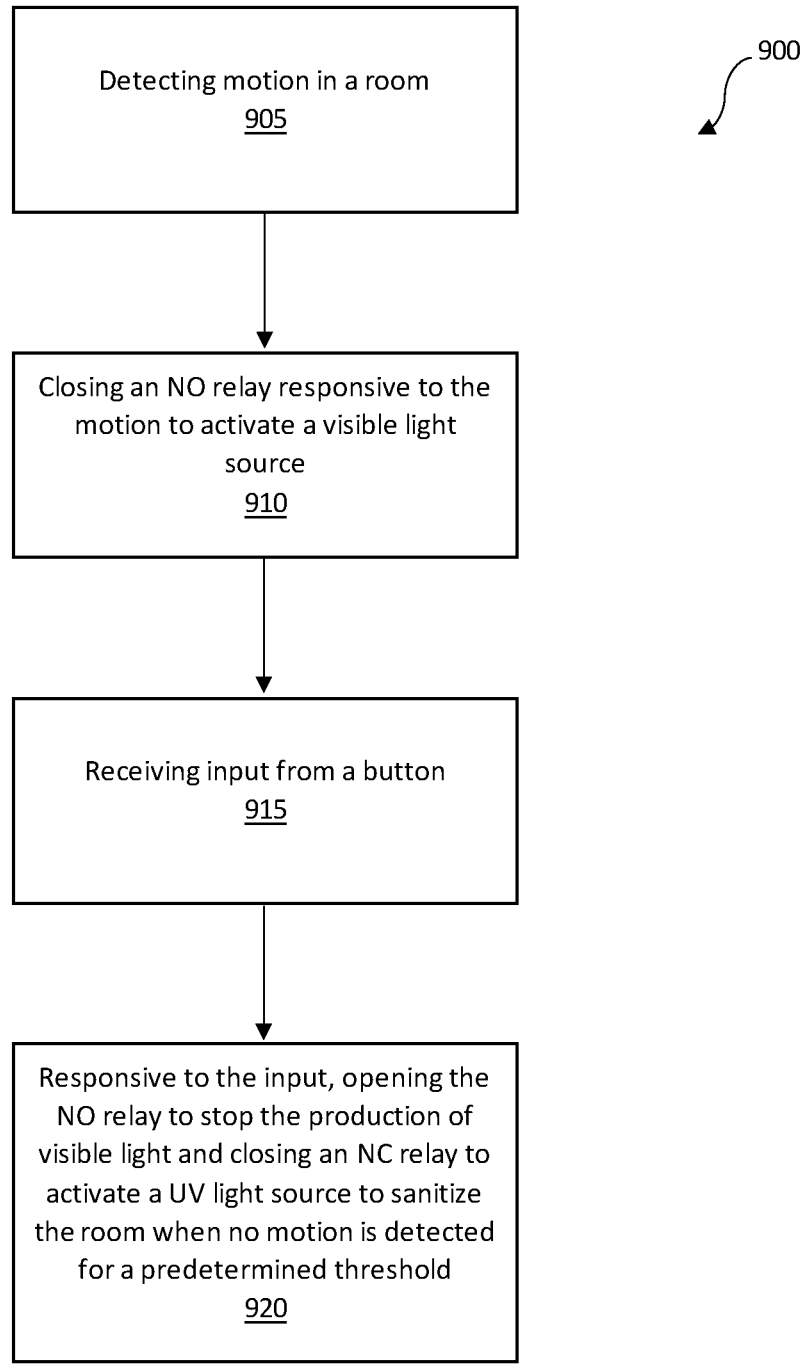
FIG. 9 depicts an exemplary sequence of steps of a process for automatically cleaning/disinfecting an environment using a motion detector coupled to NO and NC relays of a lighting assembly according to embodiments of the present invention.

FIG. 9 depicts an exemplary sequence of steps of a process 900 for automatically cleaning/disinfecting an environment (e.g., room) using a motion detector coupled to NO and NC relays of a lighting assembly according to embodiments of the present invention. The lighting assembly can be overhead lighting disposed in a home, store, or office building, for example, and includes a physical input button for activating UV light. Process 900 can be computer or electronic controlled, e.g., by a state-machine, processor, microcontroller, combinatorial logic, sequential circuits, or any suitable electronic control mechanism or combination of the above.

At step 905, motion is detected by a motion sensor coupled to an NO relay and an NC relay that conduct power to different light sources. The NO relay is coupled to a light source operable to produce visible light, and the NC relay is coupled to a light source operable to produce UV light for sanitation purposes.

At step 910, the NO relay is closed responsive to the motion detected in step 910 to produce visible light.

At step 915, input is received from a wall-mounted button, wireless device, or the like, that indicates that UV light should be produced by the lighting assembly. The input may be from an occupant pressing the button. However, the UV light is not activated immediately due to potential safety risks to the occupants.

At step 920, the NO relay is opened to deactivate the visible light source and the NC relay is closed to activate the UV light source only when no motion is detected for a predetermined threshold after the input is received at step 915. If no motion is detected for the predetermined threshold period after the button press, then the UV light source is activated. Step 920 can include starting one or more timers: 1) to set a countdown duration that expires before the UV lights are activated, and 2) to control the duration of UV light exposure. The UV light exposure typically lasts for 30-45 minutes to significantly disinfect the environment. The UV light source can be immediately deactivated when motion is detected by the sensor, or when input is received from an optional kill switch, according to embodiments. Step 920 can also include providing a visual indication that the UV light source is active, for example, by activating an LED or sending a notification to a wireless device.

Figure 10:
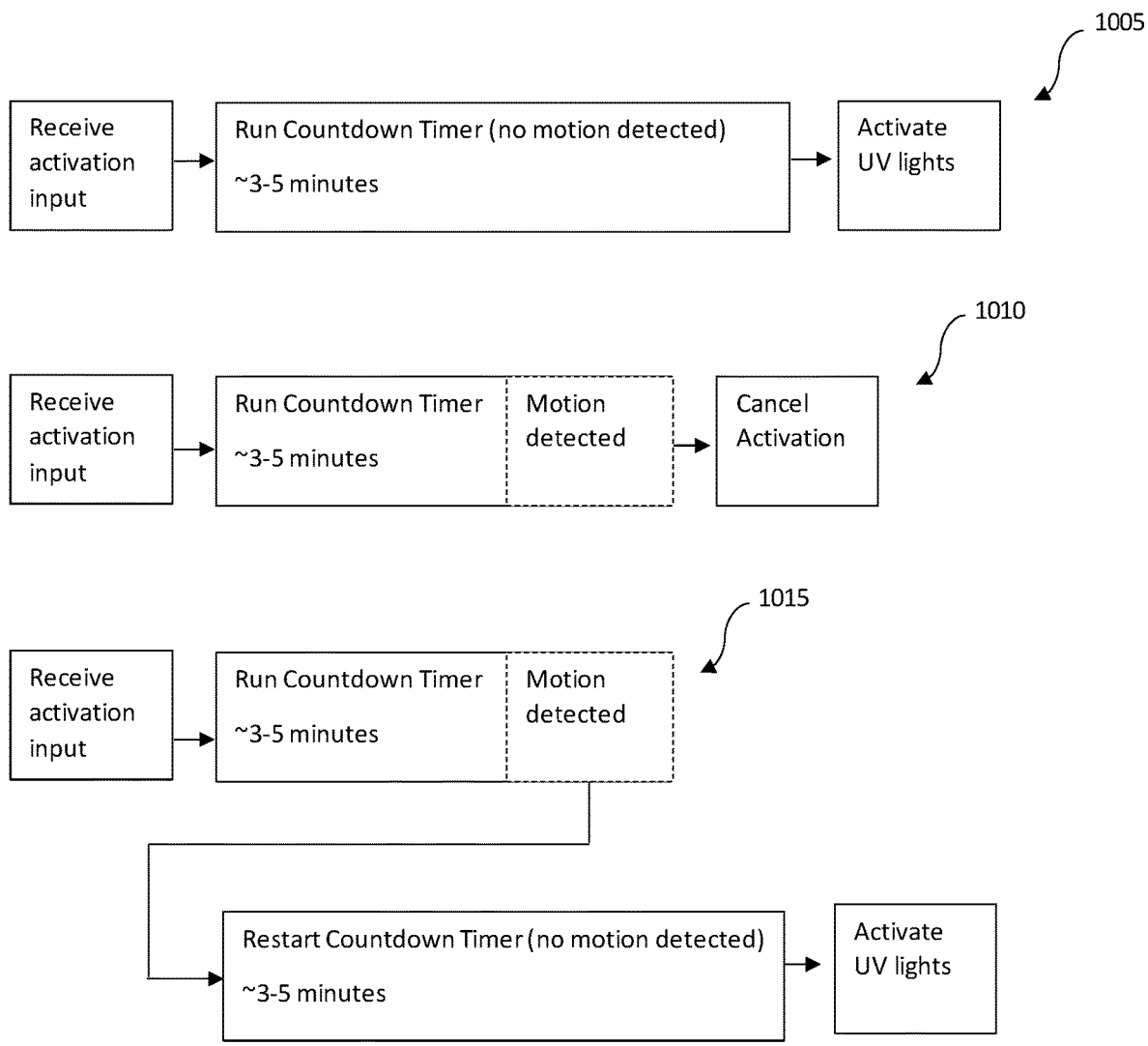
FIG. 10 is a block timing diagram depicting exemplary approaches to motion-based UV light activation according to embodiments of the present invention.

FIG. 10 is a block timing diagram depicting exemplary steps for motion-based UV light activation according to embodiments of the present invention. In process 1005, receiving activation input starts a countdown timer, which is typically configured for approximately 3-5 minutes. When no motion has been detected and the countdown timer expires, the UV lights are activated. In process 1010, receiving activation input starts a countdown timer, and detecting motion before the countdown expires causes the activation of the UV lights to be canceled. In process 1015, receiving activation input starts a countdown timer, and detecting motion before the countdown expires causes the countdown timer to be restarted. This process can be repeated any number of times until no motion is detected during the countdown period (e.g., 3-5 minutes), in which case the UV lights are activated.

Figure 11:
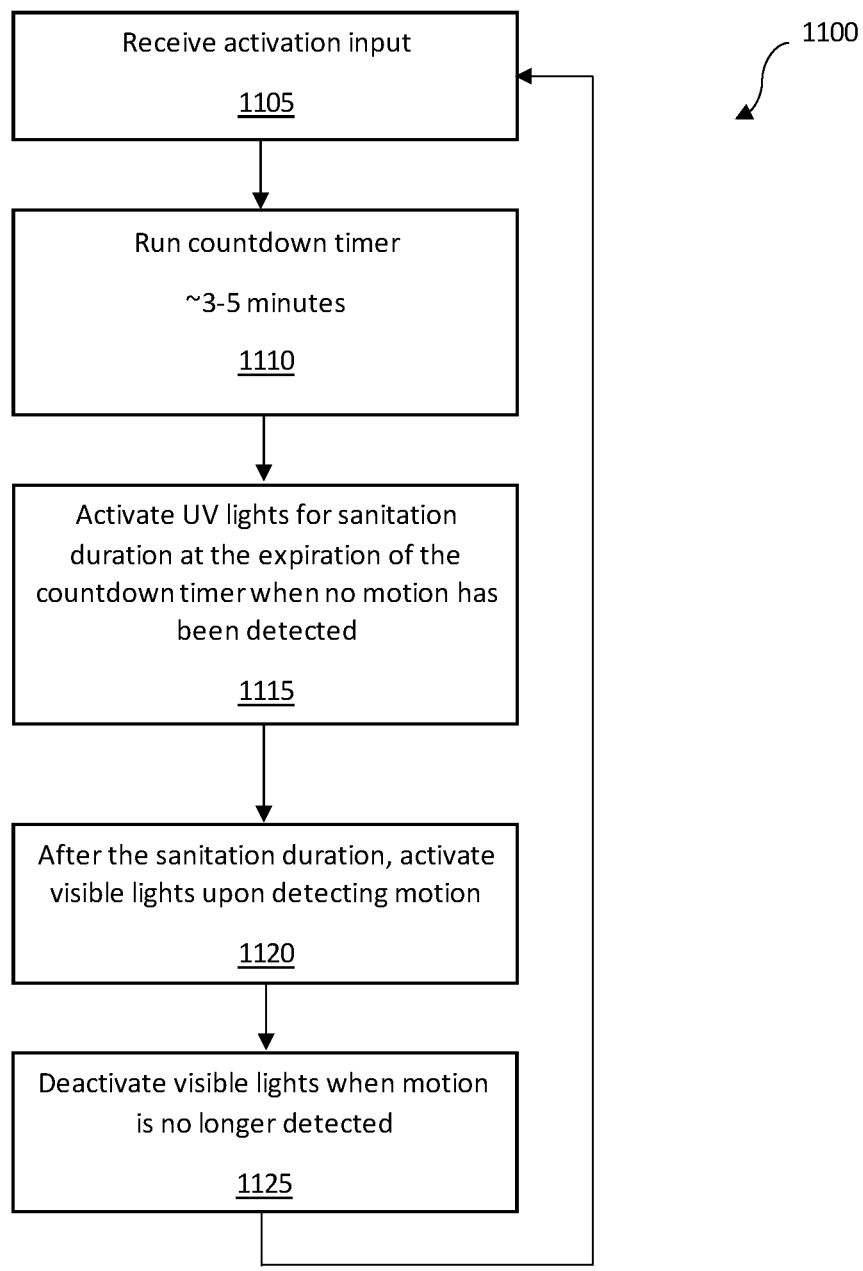
FIG. 11 depicts an exemplary sequence of steps of a process for automatically activating UV lights to clean/disinfect an environment (e.g., room) using a motion detector coupled to NO and NC relays of a lighting assembly according to embodiments of the present invention.

FIG. 11 depicts an exemplary sequence of steps of a process 1100 for automatically activating UV lights to clean/disinfect an environment (e.g., room) using a motion detector coupled to NO and NC relays of a lighting assembly according to embodiments of the present invention. The lighting assembly can be overhead lighting disposed in a home, store, or office building, for example, and includes a physical input device for activating UV light. Process 1100 can be computer or electronic controlled, e.g., by a state-machine, processor, microcontroller, combinatorial logic, sequential circuits, or any suitable electronic control mechanism or combination of the above.

At step 1105, an activation input is received at a physical input device (e.g., a wall-mounted button or switch) or a wireless device (e.g., smartphone). The input received indicates that the UV lights are to be activated.

At step 1110, a countdown timer is started that typically lasts for 3-5 minutes to prevent UV light exposure to any occupants of the room or environment.

At step 1115, when no motion has been detected during the countdown timer, the UV lights are activated for a sanitation duration when the countdown timer expires to clean/disinfect the room.

At step 1120, after the sanitation duration, the UV lights are deactivated, and visible lights activate upon detecting motion.

At step 1125, the visible lights are deactivated when motion is no longer detected, and process 1100 returns to step 1105 when another activation input is received.

Embodiments of the present invention are thus described. While the present invention has been described in particular embodiments, it should be appreciated that the present invention should not be construed as limited by such embodiments, but rather construed according to the following claims.

What is claimed is:

1. A lighting assembly comprising:
a first light source configured to produce visible light;
a second light source configured to produce ultraviolet (UV) light; and
control circuitry for selectively powering the first light source and the second light source, said control circuitry comprising:
a motion sensor; and
an input device;
wherein the control circuitry automatically deactivates the first light source and activates the second light source for a sanitation duration when the motion sensor does not detect motion for a predetermined threshold period after an input is received at the input device.

2. The lighting assembly of claim 1, wherein the first and second light sources are disposed within a housing and operable to be mounted as an overhead lighting assembly for installation in a ceiling of an indoor environment.

3. The lighting assembly of claim 1, wherein the first light source comprises at least one of: a plurality of fluorescent lights and a plurality of visible light LED lights.

4. The lighting assembly of claim 3, wherein the second light source comprises a UV LED emitter.

5. The lighting assembly of claim 1, wherein the input device comprises a wall-mounted button and a housing, and wherein the motion detector is integrated into the housing.

6. The lighting assembly of claim 1, further comprising:
a timer, and wherein the sanitation duration of the second light source is controlled by the timer; and
a visual indicator operable to provide an indication that second light source is active.

7. The lighting assembly of claim 6, wherein the timer prevents activation of the second light source for a predetermined threshold period following activation of the input device even if no motion is detected by the motion sensor for a predetermined threshold.

8. The lighting assembly of claim 1, wherein the control circuitry further comprises:

a normally open (NO) relay coupled to the first light source; and
a normally closed (NC) relay coupled to the second light source, and wherein the motion sensor is operable to selectively open and close the NO relay and the NC relay.

9. A method of activating a visible light source and an ultraviolet (UV) light source of a lighting assembly, the method comprising:
detecting motion using a motion detector;
closing a first relay of the lighting assembly to power the visible light source of the lighting assembly responsive to the detecting;
receiving an input at an input device; and
opening the first relay to deactivate the visible light source and closing a second relay to activate the UV light source responsive to the input when no motion is detected by the motion detector for a predetermined threshold time following the receiving of the input.

10. The method of claim 9, wherein the lighting assembly is operable to be an overhead lighting assembly for installation in a ceiling of an indoor environment.

11. The method of claim 9, wherein the visible light source comprises at least one of:
a plurality of fluorescent lights and a plurality of visible light LED lights.

12. The method of claim 11, wherein the UV light source comprises a UV LED emitter.

13. The method of claim 9, wherein the input device comprises a wall-mounted button and a housing, and wherein the motion detector is integrated into the housing.

14. The method of claim 9, wherein the first relay comprises a normally open (NO) relay, and wherein the second relay comprises a normally closed (NC) relay.

15. The method of claim 9, further comprising:
receiving a second input at a switch coupled to the lighting assembly; and
deactivating the visible light source and the UV light source responsive to the receiving the second input.

16. The method of claim 9, wherein the predetermined threshold time is controlled by an electronic timer coupled to the lighting assembly, and further comprising illuminating a visual indicator during the predetermined threshold time and when the UV light source is active.

17. A lighting assembly comprising:
a first light source configured to produce a first light type;
a second light source configured to produce a second light type; and
control circuitry for selectively powering the first light source and the second light source, said control circuitry comprising:
a motion sensor;
a first relay coupled to the first light source;
a second relay coupled to the second light source;
a wireless transceiver; and
a timer,
wherein the control circuitry automatically receives an activation signal from a wireless device using the wireless transceiver, starts the timer for a timer duration, opens the first relay to deactivate the first light source, and closes the second relay to power the second light source when the second relay is closed only after the timer expires, and no motion is detected by the motion sensor after the activation signal is received and over the timer duration.

18. The lighting assembly of claim 17, wherein the control circuitry automatically transmits an indication that the second light source is active to the wireless device using the wireless transceiver.

19. The lighting assembly of claim 17, wherein the wireless transceiver is operable to receive configuration data from the wireless device to configure the timer.

20. The lighting assembly of claim 17, wherein the wireless transceiver is operable to receive a deactivation signal that deactivates the second light source.

* * * * *